United States Patent [19]

Kingsley et al.

[11] 4,145,438
[45] Mar. 20, 1979

[54] METHOD FOR TREATMENT OF ECZEMA OR PSORIASIS

[75] Inventors: Patrick J. Kingsley, Loughborough; Thomas S. C. Orr, Melton Mowbray, both of England

[73] Assignee: Fisons Limited, London, England

[21] Appl. No.: 843,714

[22] Filed: Oct. 20, 1977

Related U.S. Application Data

[62] Division of Ser. No. 717,875, Aug. 26, 1976, Pat. No. 4,067,992.

[30] Foreign Application Priority Data

Sep. 10, 1975 [GB] United Kingdom ............... 37183/75
Sep. 10, 1975 [GB] United Kingdom ............... 37185/75

[51] Int. Cl.² ............................................. A61K 31/35
[52] U.S. Cl. .................................................... 424/283
[58] Field of Search ........................................ 424/283

[56] References Cited

U.S. PATENT DOCUMENTS

| | | |
|---|---|---|
| 3,419,578 | 12/1968 | Fitzmaurice et al. ................ 424/283 |
| 3,843,687 | 10/1974 | Pefferi ................................... 424/283 |

*Primary Examiner*—Stanley J. Friedman
*Attorney, Agent, or Firm*—Merriam, Marshall & Bicknell

[57] ABSTRACT

There is described a method of treatment of certain skin conditions, which method comprises per os administration of a compound of the formula I

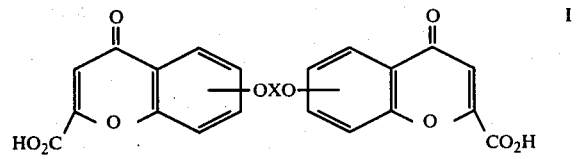

or a therapeutically acceptable salt, ester or amide thereof, wherein X is a polymethylene chain containing 3 to 7 carbon atoms inclusive, which chain may be substituted by an —OH group, (as active ingredient), to a patient having such a condition.

10 Claims, No Drawings

METHOD FOR TREATMENT OF ECZEMA OR PSORIASIS

This is a continuation, division of application Ser. No. 717,875, filed Aug. 26, 1976, now U.S. Pat. No. 4,067,992.

This invention relates to a new therapeutic method.

According to the invention there is provided a method of treatment of certain skin conditions, which method comprises per os administration of a compound of the formula I,

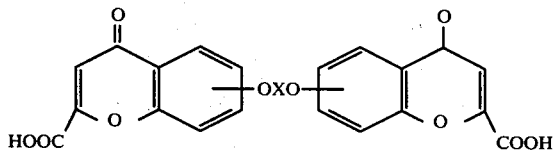

or a therapeutically acceptable salt, alkyl C 1 to 10 ester, mono-alkyl C 1 to 10 amide, di-alkyl C 1 to 10 amide or an unsubstituted amide thereof, wherein X is a polymethylene chain containing 3 to 7 carbon atoms inclusive, which chain may be substituted by an -OH group, (as active ingredient), to a patient suffering, or liable to suffer, from such a condition.

Suitable pharmaceutically acceptable salts include, for example, ammonium salts, alkali metal salts (e.g. sodium, potassium and lithium), alkaline earth metal salts (e.g. magnesium and calcium), and salts with organic amines (e.g. mono- di- or tri- alkyl C 1 to 6 amines, piperidine, and trialkanol C 1 to 6 amine salts). Esters which may be mentioned include simple alkyl esters (e.g. methyl, ethyl, propyl, isopropyl, butyl and tertiary butyl esters) and amides which may be mentioned include simple amides (for example amides with ammonia and lower alkylamines such as methylamine, ethylamine etc).

The drug may be administered to mammals, particularly humans.

The drug may be administered as a conventional, e.g. oral, composition.

In order to produce suitable compositions the drug is worked up with inorganic or organic pharmaceutically acceptable adjuvants or excipients. Examples of such adjuvants are:

For tablets and dragees: Binders, for example, cellulosic materials, e.g. microcrystalline cellulose and methyl cellulose; disintegrating agents, for example starches, e.g. maize starch; stabilisers, e.g. against hydrolysis of the active ingredients; flavouring agents, for example sugars such as lactose; fillers; stearates and inorganic diluents, e.g. talc.

For syrups, suspensions or dispersions: A liquid vehicle in which the active ingredients may be dissolved or suspended, e.g. water; and suspending agents, e.g. cellulose derivatives, gums etc.

For hard or soft capsules: diluents, e.g. lactose; glidants, e.g. stearates; inorganic materials, e.g. silica or talc; stabilisers and dispersing agents.

The composition may also contain further adjuvants, for example a composition for use in tablets may contain lubricants and glidants to assist in tabletting, e.g. magnesium stearate, or wetting agents to assist in granulation, e.g. dioctyl sodium sulphosuccinate. The composition may also if desired contain a pharmaceutically acceptable dye or colourant, and may, if desired, be coated using conventional film or sugar coating techniques.

If desired the composition may be formulated in sustained release form, e.g. by coating the drug particles themselves or granules thereof made with for example sucrose and of a size up to 2mm in diameter with a layer of e.g., beeswax, Carnauba wax, stearic or palmitic acids, cetyl alcohol or similar substances which could be expected to be slowly dissolved or digested or to act as semi-permeable membranes through which drug can diffuse when the preparations are ingested. The composition may contain drug particles or granules which are uncoated in admixture with particles or granules having one or more coats of the coating medium, and may be in the form of a capsule containing the particles or granules or alternatively a tablet, for which other adjuvants may be required, such as glidants or lubricants. The drug may be administered as an enteric coated composition to make the drug available at the appropriate part of the gastro-intestinal tract. This may be achieved by coating the tablet with a continuous film of material which is resistant and impermeable to gastric secretions, but which is susceptible to intestinal secretions. Typical film materials are shellac and its derivatives and cellulose acetate phthalate.

The drug may, if desired, be used in a specific form, e.g. having a substantial number of particles of effective particle size of less than 10 microns or particular crystal habit.

The drug may also be formulated as an aqueous, e.g. a water: chloroform (400:1), solution containing from 0.001 to 10.0% by weight of the drug. The free acids of formula I may conveniently be administered as an aqueous suspension containing from 0.1 to 10%, e.g. about 2% by weight of the drug.

The dosage to be administered will of course vary with the condition to be treated, with its severity and with its location. However in general a dosage of from about 100 to 1,000 preferably 200 to 500 mg of the drug administered 1 to 4 times a day (i.e. a daily dosage of 100 to 4,000 mg) is found to be satisfactory. The administration preferably takes place before meals.

Specific skin conditions in which the method of treatment of the invention are useful are atopic and non-atopic eczema and psoriasis.

Specific examples of the group X are groups of the formula $-(CH_2)_5-$ and $-CH_2CHOHCH_2-$, thus we prefer X to contain from 3 to 5 carbon atoms inclusive.

The chain $-O-X-O-$ may link different or corresponding positions on the chromone nuclei. We prefer the $-OXO-$ group to link the 5,5' positions on the chromone nuclei.

A preferred compound for use in this invention is 1,3-bis(2-carboxychromon-5-yloxy)-2-hydroxypropane, the disodium salt of which is commonly known as a disodium cromoglycate or cromolyn sodium.

The above mentioned compound may of course be used in the form of its pharmaceutically acceptable, e.g. its di-sodium, di-potassium, calcium, magnesium or di-piperidine salts. It may also be used in the form of its di-ethyl ester, or of its simple amide derived from ammonia.

The invention is illustrated, but in no way limited by the following Examples in which s.c.g. means disodium cromoglycate (cromolyn sodium).

EXAMPLE 1

Case Report On Oral Sodium Cromoglycate In The Treatment Of Eczema

Male aged 13 (date of birth - 16.2.62) with a history of eczema since three months old. Condition described as difficult to treat with conventional methods. He had a total Serum IgE of 24.000 U/ml (normal 200-400 U/ml) and positive RAST tests (class 4) against all common food stuffs.

Treatment was commenced on 23.10.75 with s.c.g. administered orally at a dose of 100 mg four times daily. Within one week the erythema was not so severe, the itching was less and his pre tibial oedema was reduced. He remained at this time on a milk free diet.

Since then he has been maintained on 100 mg s.c.g. given orally four times daily and the latest report on 8.6.76 was that he remained well.

EXAMPLE 2

Summary Of Clinical Trial Of Oral Sodium Cromoglycate In The Treatment Of Eczema, Asthma And Rhinitis Twenty children aged between 1 year and 16 years were treated orally for three weeks with either s.c.g. or matching placebo on a double blind randomised basis. After three weeks they took the alternative treatment for three weeks. Of the twenty children five had asthma, seven had rhinitis and fourteen had eczema which was severe in seven. At the end of the study in the opinion of the parents thirteen preferred the active preparation, three the placebo and there was no difference in four. Seven of the fourteen cases with eczema had relief of symptoms on active drug.

We claim:

1. A method of treatment of eczema or of psoriasis, which method comprises per os administration in an amount effective to ameliorate the symptoms thereof, of a compound of formula I,

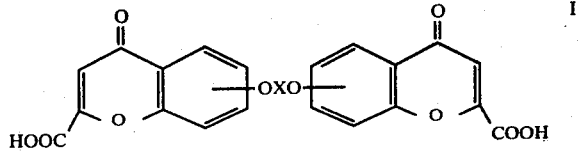

wherein X is a polymethylene chain containing 3 to 7 carbon atoms inclusive, which chain may be substituted by an -OH group, or a therapeutically acceptable salt, alkyl C 1 to 10 ester, mono-alkyl C 1 to 10 amide, di-alkyl C 1 to 10 amide or an unsubstituted amide thereof, to a patient suffering from such a condition.

2. A method according to claim 1, wherein X contains from 3 to 5 carbon atoms inclusive.

3. A method according to claim 1, wherein X is $-CH_2CHOHCH_2-$.

4. A method according to claim 1, wherein the $-OXO-$ chain links the 5,5' positions on the chromone nuclei.

5. A method according to claim 1, wherein the compound of formula I is 1,3-bis(2-carboxychromon-5-yloxy)-2-hydroxypropane or a pharmaceutically acceptable salt thereof.

6. A method according to claim 5, wherein the compound of formula I is the disodium salt of 1,3-bis(2-carboxychromon-5-yloxy)-2-hydroxypropane.

7. A method according to claim 1, wherein the condition is eczema.

8. A method according to claim 1, wherein from 100 to 4,000 of active ingredient per day are administered to the patient.

9. A method according to claim 1, wherein from 200 to 500 mg of active ingredient are administered 1 to 4 times a day to the patient.

10. A method according to claim 1, wherein the active ingredient is administered orally before a meal.